US011478160B2

(12) United States Patent
Deno et al.

(10) Patent No.: US 11,478,160 B2
(45) Date of Patent: Oct. 25, 2022

(54) VITAL INFORMATION MEASURING APPARATUS, METHOD, AND PROGRAM

(71) Applicant: OMRON HEALTHCARE CO., LTD., Muko (JP)

(72) Inventors: Toru Deno, Kyoto (JP); Naoki Tsuchiya, Tokyo (JP); Hiroshi Usui, Kyoto (JP); Kosuke Inoue, Kyoto (JP); Yoshiyuki Morita, Nagaokakyo (JP); Yasushi Matsuoka, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 309 days.

(21) Appl. No.: 16/910,178

(22) Filed: Jun. 24, 2020

(65) Prior Publication Data
US 2020/0323441 A1    Oct. 15, 2020

Related U.S. Application Data

(63) Continuation of application No. PCT/JP2018/046239, filed on Dec. 17, 2018.

(30) Foreign Application Priority Data

Dec. 27, 2017    (JP) .............................. JP2017-252652

(51) Int. Cl.
*A61B 5/00*    (2006.01)
*A61B 5/021*   (2006.01)
(Continued)

(52) U.S. Cl.
CPC ........ *A61B 5/02141* (2013.01); *A61B 5/0235* (2013.01); *A61B 5/1116* (2013.01);
(Continued)

(58) Field of Classification Search
CPC ... A61B 5/02141; A61B 5/0235; A61B 5/116; A61B 5/681; A61B 5/746; A61B 2562/0247; A61B 5/0225; A61B 5/02233
See application file for complete search history.

(56) References Cited

U.S. PATENT DOCUMENTS 4,313,445 A * 2/1982 Georgi ................... A61B 7/045
                                                        600/495
5,556,415 A * 9/1996 McEwen .............. A61B 5/7435
                                                        600/499
(Continued)

FOREIGN PATENT DOCUMENTS

JP    2002-034937 A    2/2002
JP     2017-6230 A     1/2017
(Continued)

OTHER PUBLICATIONS

Jun. 30, 2020 International Preliminary Report on Patentability issued in International Patent Application No. PCT/JP2018/046239.
(Continued)

*Primary Examiner* — Ojiako K Nwugo
(74) *Attorney, Agent, or Firm* — Oliff PLC

(57) ABSTRACT

A vital information measuring apparatus according to an aspect of the present invention is a vital information measuring apparatus for measuring vital information by compressing a measurement site of a subject with a cuff, and includes a fluid supply unit configured to supply a fluid to the cuff, and a first fluid supply controller configured to control, when a situation of the subject satisfies a first condition in which measurement of the vital information is recommended, a supply of the fluid to the cuff by the fluid supply unit to compress the measurement site in a first compression mode for informing the subject that the first condition is satisfied.

12 Claims, 8 Drawing Sheets

(51) Int. Cl.
*A61B 5/0235* (2006.01)
*A61B 5/11* (2006.01)

(52) U.S. Cl.
CPC .............. *A61B 5/681* (2013.01); *A61B 5/746* (2013.01); *A61B 2562/0247* (2013.01)

(56) References Cited

U.S. PATENT DOCUMENTS

| | | | | |
|---|---|---|---|---|
| 5,855,589 | A * | 1/1999 | McEwen | A61B 5/02233 600/499 |
| 6,544,202 | B2 * | 4/2003 | McEwen | A61H 9/0078 601/150 |
| 8,197,414 | B2 * | 6/2012 | Quinn | A61B 5/02225 600/490 |
| 8,840,561 | B2 * | 9/2014 | Lane | A61B 5/0225 600/495 |
| 9,750,419 | B2 * | 9/2017 | Whitaker | A61B 5/022 |
| 2007/0185401 | A1 * | 8/2007 | Quinn | A61B 5/0225 600/490 |
| 2010/0191277 | A1 * | 7/2010 | McEwen | A61B 17/1355 606/202 |
| 2011/0237963 | A1 | 9/2011 | Nishioka et al. | |
| 2012/0259216 | A1 * | 10/2012 | Gerrans | A61B 17/22 604/514 |
| 2015/0272452 | A1 * | 10/2015 | Mullin | A61B 5/02233 600/301 |
| 2018/0042501 | A1 * | 2/2018 | Adi | A61B 5/7246 |
| 2018/0235488 | A1 * | 8/2018 | Aelen | A61B 5/02225 |

FOREIGN PATENT DOCUMENTS

| | | |
|---|---|---|
| WO | 2010/067723 A1 | 6/2010 |
| WO | 2012/018029 A1 | 2/2012 |

OTHER PUBLICATIONS

Feb. 26, 2019 International Search Report issued in International Patent Application No. PCT/JP2018/046239.

* cited by examiner

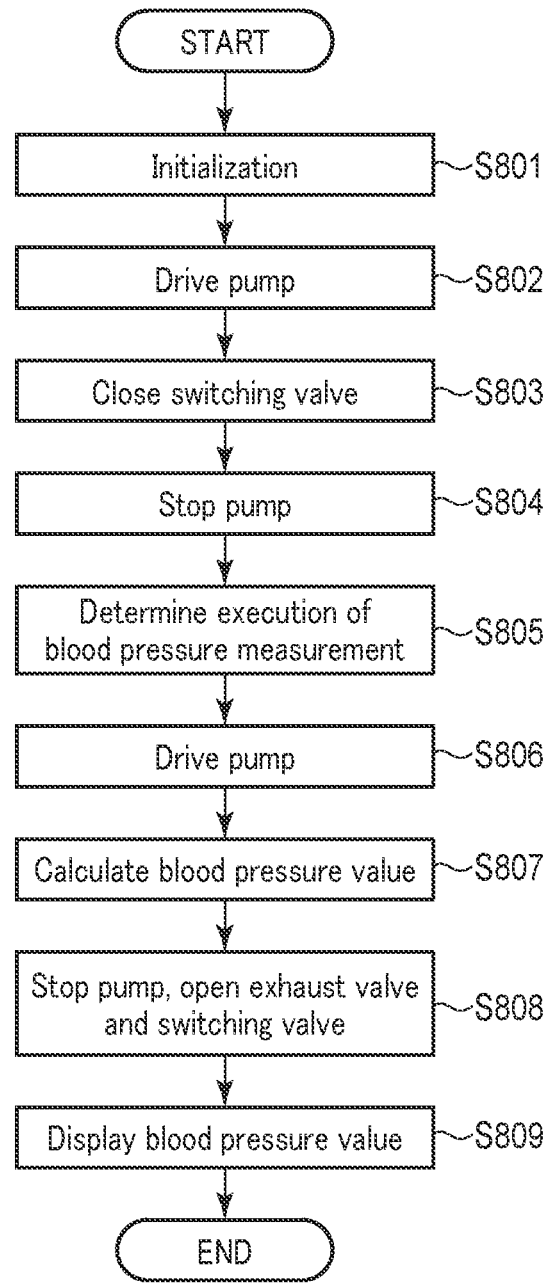
F I G. 8

VITAL INFORMATION MEASURING APPARATUS, METHOD, AND PROGRAM

CROSS-REFERENCE TO RELATED APPLICATIONS

This application is a Continuation Application of PCT Application No. PCT/JP2018/046239, filed Dec. 17, 2018 and based upon and claiming the benefit of priority from Japanese Patent Application No. 2017-252652, filed Dec. 27, 2017, the entire contents of all of which are incorporated herein by reference.

FIELD

The present invention relates to a vital information measuring apparatus for measuring vital information such as blood pressure, a method therefor, and a program therefor.

BACKGROUND

In recent years, for example, there has been an increase in the number of people who measure vital information such as blood pressure at home for health management. Blood pressure changes greatly throughout a day. Therefore, it is recommended that blood pressure be measured at a fixed time every day, for example, after waking up, before going to bed, etc.

In addition, there has been increasing attention to a phenomenon of hypertension occurring during a stay at a particular location. For example, there is a phenomenon of so-called workplace hypertension in which blood pressure is higher at the workplace while it is normal outside the workplace. Therefore, in order to check whether a user has workplace hypertension, it is necessary to measure the blood pressure while at the workplace.

Meanwhile, in recent years, wearable vital information measuring apparatuses have been developed. For example, Jpn. Pat. Appln. KOKAI Publication No 2017-6230 discloses a wristwatch-type vital information measuring apparatus. When a wearable vital information measuring apparatus is used, a user can easily measure his or her vital information at a place away from home such as a workplace.

The vital information measuring apparatus disclosed in Jpn. Pat. Appln. KOKAI Publication No 2017-6230 is configured to start measurement of vital information in response to a user's operation of a measurement start instruction. In other words, whether to execute the vital information measurement is left to the user. Therefore, for example, if the user forgets to perform the measurement start operation, the vital information measurement is not performed in a situation where the vital information measurement is recommended, for example, at a time or place designated in advance, causing deficiency in measurement data.

SUMMARY

A vital information measuring apparatus according to one aspect of the present invention is a vital information measuring apparatus for measuring vital information by compressing a measurement site of a subject with a cuff, and includes a fluid supply unit configured to supply a fluid to the cuff, and a first fluid supply controller configured to control, when a situation of the subject satisfies a first condition in which measurement of the vital information is recommended, a supply of the fluid to the cuff by the fluid supply unit to compress the measurement site in a first compression mode for informing the subject that the first condition is satisfied.

According to the configuration, when the subject's situation satisfies the first condition in which the vital information measurement is recommended, the subject is notified accordingly by compression with a cuff. Therefore, the subject can reliably recognize that the situation in which measurement is recommended has been reached. Moreover, since notification is given by inflation of the cuff, which is already provided for measurement, it is not necessary to provide other notification means such as light, sound, vibration, etc.

In the vital information measuring apparatus according to the aspect, when at least one of a predetermined time of day, place, or event is satisfied as the first condition, the first fluid supply controller may perform control for compressing the measurement site in the first compression mode. According to the configuration, if at least one of a preset time of day, place, or event is satisfied, notification is given to prompt measurement of the vital information.

The vital information measuring apparatus according to the aspect may further include a second fluid supply controller configured to control, when a second condition indicating that the subject is in a measurable state is satisfied after the control by the first fluid supply controller, the supply of the fluid to the cuff by the fluid supply unit to compress the measurement site in a second compression mode for measuring the vital information.

According to the configuration, the vital information is measured when the subject is in a measurable state after the notification. Therefore, accurate measurement can always be performed. In addition, since a certain amount of fluid is contained in the cuff through the fluid supply by the first compression mode, the fluid supply by the second compression mode requires a smaller amount of fluid than the amount necessary for normal blood pressure measurement. That is, the time required for blood pressure measurement is shortened. As a result, it is possible to reduce a burden on the user, e.g., shortening the time during which the user maintains a measurement posture.

In the vital information measuring apparatus according to the aspect, the first fluid supply controller may set the first compression mode to a pressure value smaller than that of the second compression mode by the second fluid supply controller.

According to the configuration, the cuff pressure at the time of the notification is set to a value smaller than that at the time of measurement. Therefore, the notification can be made without applying a large physical load to the subject, and an electric power consumed for inflating the cuff for the notification can be reduced.

In the vital information measuring apparatus according to the aspect, the cuff may include a first fluid bladder and a second fluid bladder, the first fluid supply controller may control the fluid supply unit to supply the fluid to one of the first fluid bladder or the second fluid bladder, and the second fluid supply controller may control the fluid supply unit to supply the fluid to both the first fluid bladder and the second fluid bladder.

According to the configuration, the notification and the measurement can be distinguished from each other by selection of the fluid bladders, and thus it is not necessary to differentiate pressures between the notification and the measurement as in the case of using one fluid bladder, for example.

The vital information measuring apparatus according to the aspect may further include a posture detection unit configured to detect a posture of the subject. When, as the second condition, the posture detection unit detects that the posture of the subject is a predetermined posture in which measurement can be taken, the second fluid supply controller may perform control for compressing the measurement site in the second compression mode.

According to the configuration, since the measurement is performed when the posture of the subject becomes a posture in which measurement can be taken, the measurement can always be performed when the posture of the subject is in an appropriate state.

The vital information measuring apparatus according to the aspect may further include a posture correction notification unit configured to notify the subject to correct the posture of the subject when the posture detection unit detects that the posture of the subject is different from the posture in which measurement can be taken. According to the configuration, it is possible to prompt the subject to take a posture suitable for measurement.

The vital information measuring apparatus according to the aspect may further include an input detection unit configured to detect an input of operation information indicating that the subject is in a measurable state. When, as the second condition, the input detection unit detects the input of operation information, the second fluid supply controller performs control for compressing the measurement site in the second compression mode.

According to the configuration, since the measurement is performed when the operation information indicating that the subject is in a measurable state is input, the measurement can be performed, for example, after the subject is in an environment or timing suitable for the measurement.

In the vital information measuring apparatus according to the aspect, when the second condition is not satisfied within a predetermined time period after the control for compressing the measurement site in the first compression mode, the first fluid supply controller may perform the control for compressing the measurement site in the first compression mode again.

According to the configuration, when the subject is not in a measurable state even after a certain period of time has elapsed after the notification, the notification is made again. Therefore, even when the subject does not notice the notification for some reason, it is possible to notify the subject that the condition in which the measurement should be conducted is satisfied.

According to the present invention, it is possible to provide a vital information measuring apparatus that enables measurement to be reliably performed under a situation in which a vital information measurement is recommended, and to provide a method of measuring vital information.

BRIEF DESCRIPTION OF THE DRAWINGS

FIG. 8 is a flowchart illustrating a series of flows from a start to a completion of blood pressure measurement.

DETAILED DESCRIPTION

Hereinafter, embodiments of the present invention will be described with reference to the accompanying drawings.

According to one embodiment of the present invention, there are provided a vital information measuring apparatus that enables measurement to be reliably performed under a situation in which a vital information measurement is recommended.

Embodiment

Figure 1:
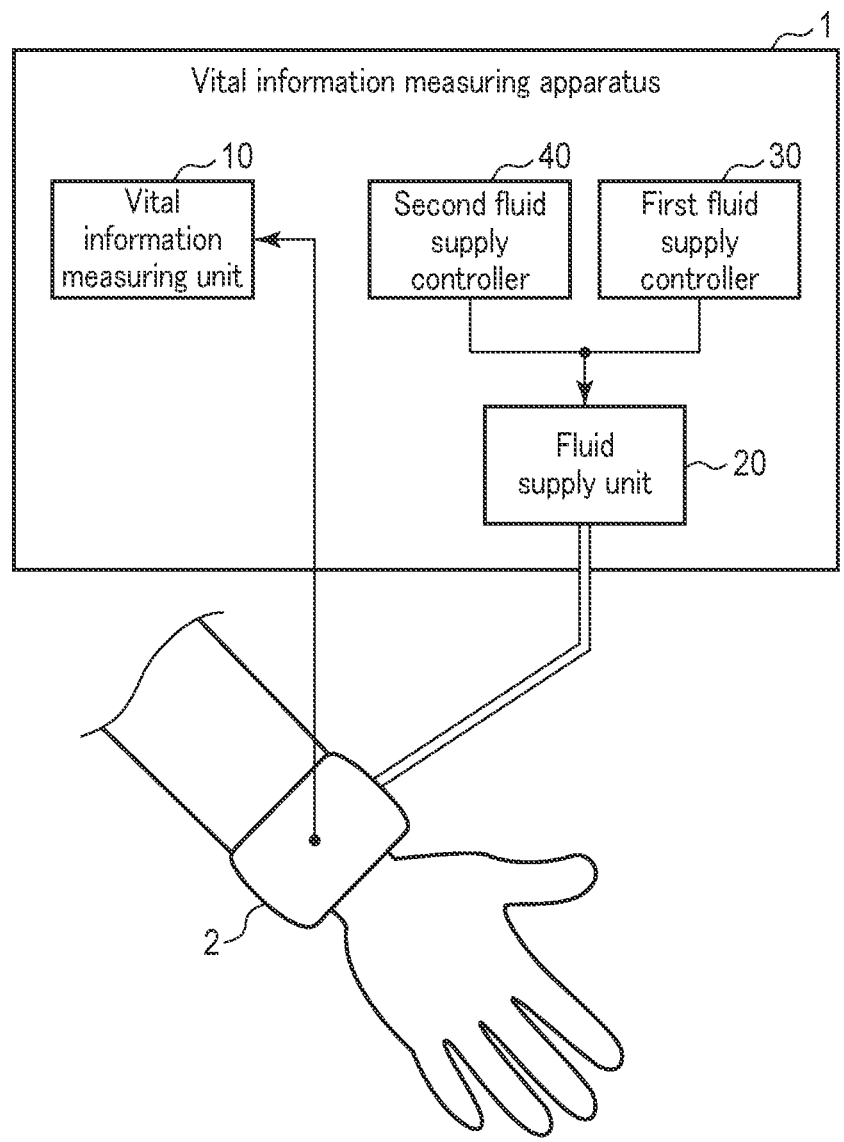
FIG. 1 is a block diagram showing a vital information measuring apparatus according to an embodiment of the present invention.

FIG. 1 is a block diagram showing a functional configuration of a vital information measuring apparatus 1 according to an embodiment of the present invention. The vital information measuring apparatus 1 is a wearable vital information measuring apparatus including a cuff 2, and is worn on a measurement site (for example, a wrist) of a user who is a subject. The vital information measuring apparatus 1 includes a vital information measuring unit 10, a fluid supply unit 20, a first fluid supply controller 30, and a second fluid supply controller 40. The cuff 2 includes one or more fluid bladders. The fluid supply unit 20 supplies a fluid to the cuff 2 to inflate the cuff 2, thereby compressing the measurement site. With the measurement site being compressed, the vital information measuring unit 10 detects a pressure of the cuff 2 by a pressure sensor (not shown), and calculates vital information based on an output of the pressure sensor. The vital information includes, but is not limited to, a blood pressure value and a pulse rate. As the fluid, air is typically used, but other gases or liquids may be used.

When a first condition, in which the user's vital information measurement is recommended, is satisfied, the first fluid supply controller 30 controls a supply of the fluid to the cuff 2 by the fluid supply unit 20 to compress the measurement site in a first compression mode for notifying the user that the first condition is satisfied. As the first condition, for example, at least one of a predetermined time of day, place, or event is assumed. The first compression mode may be, for example, a compression mode with a pressure smaller than that of a second compression mode used during the blood pressure measurement since it is enough that the user can perceive the inflation of the cuff 2.

When a second condition, representing a state in which the user can perform measurement, is satisfied after the first fluid supply controller 30 performs control by the first compression mode, the second fluid supply controller 40 controls the supply of the fluid to the cuff 2 by the fluid supply unit 20 to compress the measurement site in a second compression mode for measuring the vital information. As the second condition, for example, an assumed case may be a case where a posture detection unit detects that the user's posture is a predetermined posture in which measurement can be taken, or a case where an input of operation information indicating that the user is in a measurable situation is detected.

According to the vital information measuring apparatus of the embodiment including the configuration as described above, under the control of the first fluid supply controller 30, for example, when a current time reaches a predetermined time of day, the fluid is supplied to the cuff 2 to compress the measurement site in the first compression mode having a pressure value smaller than that at the time of measuring the vital information, and in this manner, the user is notified of being in a situation in which vital information should be measured. In addition, when the user moves to a predetermined place such as a workplace or when an event such as a meeting is conducted, the measurement site is compressed in the first compression mode in a similar manner, and the user is notified of being in a situation in which vital information should be measured. Therefore, the user can reliably recognize that the user is in a situation in which vital information should be measured. Since notification is conducted using the inflation of the cuff 2, which is already provided for measuring vital information, it is not necessary to provide other notification means such as light, sound, vibration, or the like.

Furthermore, according to the blood pressure monitor of the embodiment, the following control is performed by the second fluid supply controller 40. That is, after the user is notified of being in a situation in which the blood pressure should be measured, for example, when the user's posture becomes a predetermined posture in which measurement can be taken or the user inputs operation information indicating that the user is in a measurable state, the fluid supply unit 20 supplies the fluid to the cuff 2 to compress the measurement site in the second compression mode for measuring the vital information, and the vital information measuring unit 10 measures the blood pressure. Therefore, the vital information is measured when the user is in a measurable state. For this reason, it is possible to accurately measure the blood pressure of the user under a situation suitable for measurement at all times.

The measurement site is not limited to the wrist, and may be another site such as an upper arm.

First Embodiment (Configuration)

Figure 2:
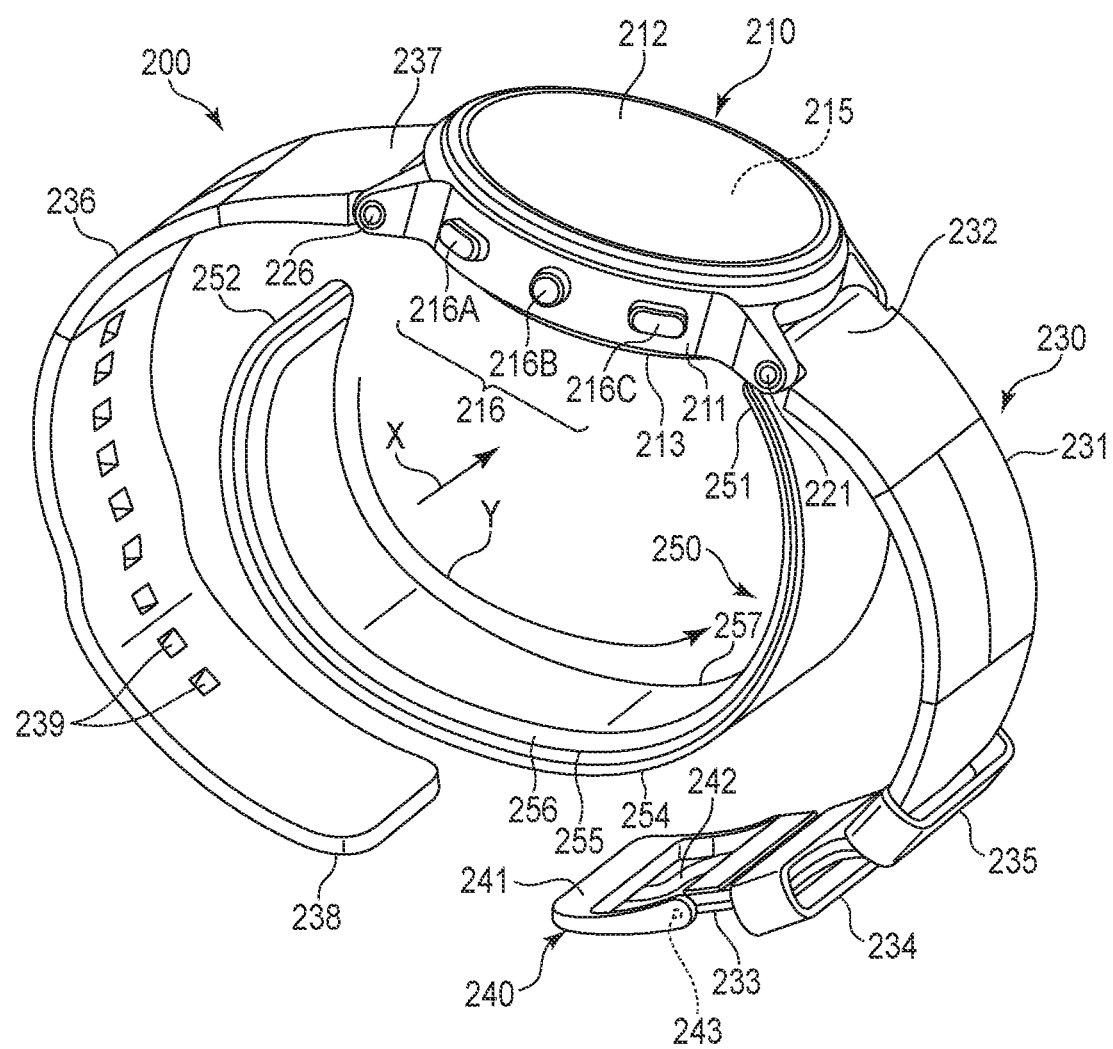
FIG. 2 is a perspective view showing an appearance of a blood pressure monitor according to a first embodiment.

FIG. 2 is a perspective view showing an appearance of a blood pressure monitor 200 according to the first embodiment. The blood pressure monitor 200 is a wristwatch-type wearable device. The blood pressure monitor 200 is designed to be worn on, for example, a left wrist of the user, and measures the blood pressure on the left wrist. The blood pressure monitor 200 includes a main body 210, a belt 230, and a cuff structure 250. The belt and cuff structure may be collectively referred to as a cuff.

The main body 210 includes a cylindrical case 211, a circular glass 212 attached to one opening of the case 211, and a back cover 213 attached to the other opening of the case 211. The case 211 has a pair of projecting lugs at two portions on the side surface for attachment of the belt 230.

Inside the main body 210, a display unit 215 is provided to face the glass 212. The display unit 215 may be a liquid crystal display (LCD), an organic light emitting diode (OLED) display, or the like. The main body 210 is provided with an operation unit 216. The operation unit 216 allows the user to input various instructions to the blood pressure monitor 200. Using the operation unit 216, the user can input an instruction to perform the blood pressure measurement or an instruction to display a history of blood pressure measurement results. In this example, the operation unit 216 includes push buttons 216A, 216B, and 216C provided on the side surface of the case 211. A touch screen may be used as a combination of the display unit 215 and the operation unit 216.

Inside the main body 210, a plurality of components are further provided including components for blood pressure measurement (hereinafter, blood pressure measurement components). These components will be described later with reference to FIG. 4.

The belt 230 is an example of a member for wearing the main body 210 around the left wrist of the user. The belt 230 includes a belt-shaped first belt portion 231 and a belt-shaped second belt portion 236. The first belt portion 231 includes a proximal part 232 rotatably attached to a pair of lugs of the main body 210 by a connecting rod 221 extending in an X direction. The X direction corresponds to a width direction of the belt 230. Similarly, the second belt portion 236 includes a proximal part 237 rotatably attached to a pair of lugs of the main body 210 by a connecting rod 226 extending in the X direction.

A buckle 240 is attached to a distal part 233 of the first belt portion 231. The buckle 240 includes a substantially squared bracket-shaped frame 241, a bar 242, and a connecting rod 243 extending in the X direction. The frame 241 and bar 242 are rotatably attached to the distal part 233 of the first belt portion 231 by the connecting rod 243. Ring-shaped belt holders 234 and 235 are provided between the distal part 233 and the proximal part 232 of the first belt portion 231. The inner circumferential surface of the first belt portion 231 does not protrude inward at the belt holders 234 and 235. This allows the belt 230 to uniformly surround the outer circumferential surface of the cuff structure 250.

A plurality of small openings 239 are formed between the proximal part 237 and the distal part 238 of the second belt portion 236 to penetrate through the second belt portion 236 in the thickness direction thereof. When the first belt portion 231 and the second belt portion 236 are fastened to each other, the second belt portion 236 is passed through the frame 241 of the buckle 240 from the distal part 238 side, and the bar 242 of the buckle 240 is passed through any one of the small openings 239 of the second belt portion 236. The distal part 238 of the second belt portion 236 is held by the belt holders 234 and 235.

The first belt portion 231 and the second belt portion 236 are formed of, for example, a plastic material. The first belt portion 231 and the second belt portion 236 are flexible in the thickness direction, and substantially non-stretchable in the longitudinal direction. Therefore, the blood pressure monitor 200 can be easily worn, and the left wrist can be easily compressed during blood pressure measurement. The first belt portion 231 and the second belt portion 236 may be formed of other materials, for example, a leather material. The frame 241 and the bar 242 of the buckle 240 are formed of, for example, a metal material. The frame 241 and the bar 242 may be formed of other materials, for example, a plastic material.

The cuff structure 250 has an elongated belt shape. The cuff structure 250 faces the inner circumferential surface of the belt 230. The cuff structure 250 has a proximal part 251 attached to the main body 210. The cuff structure 250 has a distal part 252 which is a free end. Thus, the cuff structure 250 can be freely separated from the inner circumferential surface of the belt 230.

The cuff structure 250 includes a curler 254, a pressing cuff 255 disposed along an inner circumferential surface of the curler 254, a back plate 256 disposed along an inner circumferential surface of the pressing cuff 255, and a sensing cuff 257 disposed along an inner circumferential surface of the back plate 256. When the blood pressure monitor 200 is worn by the user, the sensing cuff 257 is in contact with the left wrist. In this specification, the phrase "in contact with" includes not only direct contact but also indirect contact via another member (for example, a cover member). In the present embodiment, the belt 230, the curler 254, the pressing cuff 255, and the back plate 256 function as a pressing member capable of generating a force for pressing the sensing cuff 257 against the left wrist. The blood pressure monitor 200 compresses the left wrist by the pressing member via the sensing cuff 257.

The curler 254 is, for example, a resin plate (for example, a polypropylene plate) having a certain degree of flexibility and hardness. The curler 254 has a shape curved along a Y direction in a natural state. As a result, the shape of the cuff structure 250 in the natural state is maintained in a curved state along the Y direction. The Y direction corresponds to a circumferential direction of the left wrist.

The pressing cuff 255 is a fluid bladder capable of containing a fluid. A flexible tube 421 (shown in FIG. 4) is attached to the pressing cuff 255. The flexible tube 421 is used to supply a pressurizing fluid to the pressing cuff 255 and to exhaust the pressurizing fluid from the pressing cuff 255. When the fluid is supplied to the pressing cuff 255, the pressing cuff 255 inflates, thereby compressing the left wrist.

As an example, the pressing cuff 255 includes two bag-shaped members stacked in the thickness direction. Each bag-shaped member is formed by, for example, welding peripheral edge portions of two stretchable polyurethane sheets. A plurality of through holes are formed in the bag-shaped members in order to allow the fluid to flow between the bag-shaped members. The flexible tube 421 is attached to one of the bag-shaped members. When the fluid is supplied to the bag-shaped members via the flexible tube 421, the pressing cuff 255 presses the sensing cuff 257 against the left wrist by inflation of these bag-shaped members, thereby compressing the left wrist.

The back plate 256 is, for example, a resin plate (for example, a polypropylene plate). The back plate 256 functions as a reinforcing plate. The back plate 256 transmits the pressing force from the pressing cuff 255 to the entire sensing cuff 257. A plurality of grooves having a V-shaped or U-shaped cross section extending in the X direction are provided on the inner peripheral surface and the outer peripheral surface of the back plate 256. Accordingly, the back plate 256 is easily bent. Therefore, the back plate 256 does not prevent the cuff structure 250 from bending.

The sensing cuff 257 is a fluid bladder capable of containing a fluid. As an example, the sensing cuff 257 includes two stretchable polyurethane sheets, and peripheral portions of these polyurethane sheets are welded to form a bag shape. A flexible tube 423 (shown in FIG. 4) is attached to the sensing cuff 257. The flexible tube 423 is used to supply a pressure-transferring fluid to the sensing cuff 257 and to exhaust the pressure-transferring fluid from the sensing cuff 257.

The blood pressure monitor 200 having the above-described configuration is worn on the left wrist of the user in a state where the cuff structure 250 surrounds the left wrist and the belt 230 restrains the cuff structure 250 with respect to the left wrist.

Figure 3:
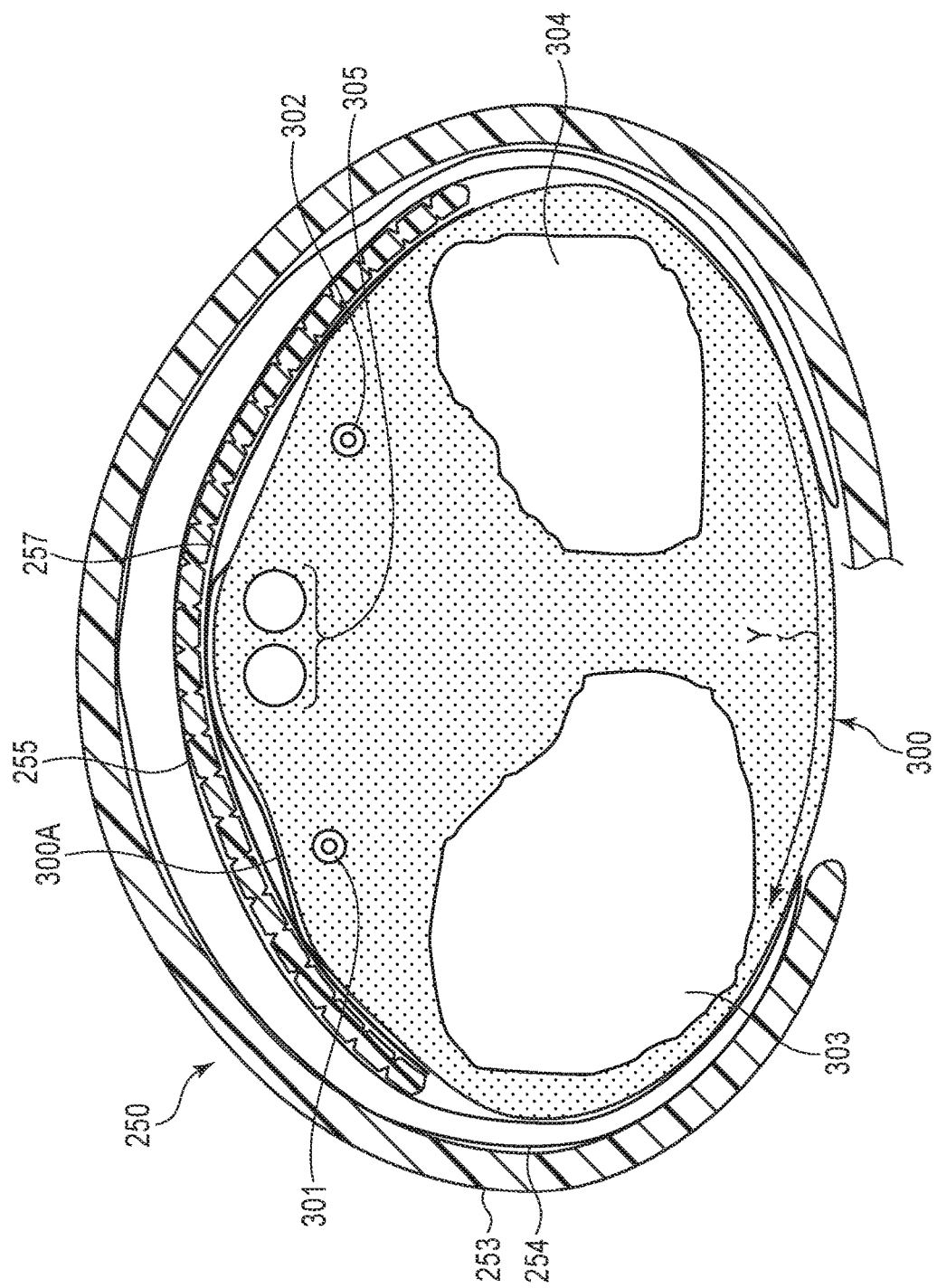
FIG. 3 is a cross-sectional view showing a cuff structure shown in FIG. 2.

FIG. 3 shows a cross section of the blood pressure monitor 200 in a state where the blood pressure monitor 200 is worn on the left wrist 300 (hereinafter, a worn state). This cross section corresponds to a cross section perpendicular to the X direction shown in FIG. 2. In FIG. 3, the main body 210 and the belt 230 are omitted. FIG. 3 shows a radial artery 301, ulnar artery 302, radius 303, ulna 304, and tendon 305 of the left wrist 300.

In the worn state, the curler 254 extends along the Y direction (corresponding to the circumferential direction of the left wrist 300). The pressing cuff 255 extends along the Y direction on the inner circumferential side of the curler 254. The back plate 256 extends along the Y direction on the inner circumferential side of the pressing cuff 255. The sensing cuff 257 is disposed on the inner circumferential side of the back plate 256, is in contact with the left wrist 300, and extends along the Y direction so as to cross an artery passage portion 300A of the left wrist 300.

The blood pressure monitor 200 employs a double cuff structure having the pressing cuff 255 and the sensing cuff 257, and the left wrist is compressed by the sensing cuff 257 by a pressing force from the pressing cuff 255. This makes it possible to effectively compress the artery (for example, the radial artery 301) passing through the left wrist 300. As a result, the blood pressure can be measured with high accuracy.

Figure 4:
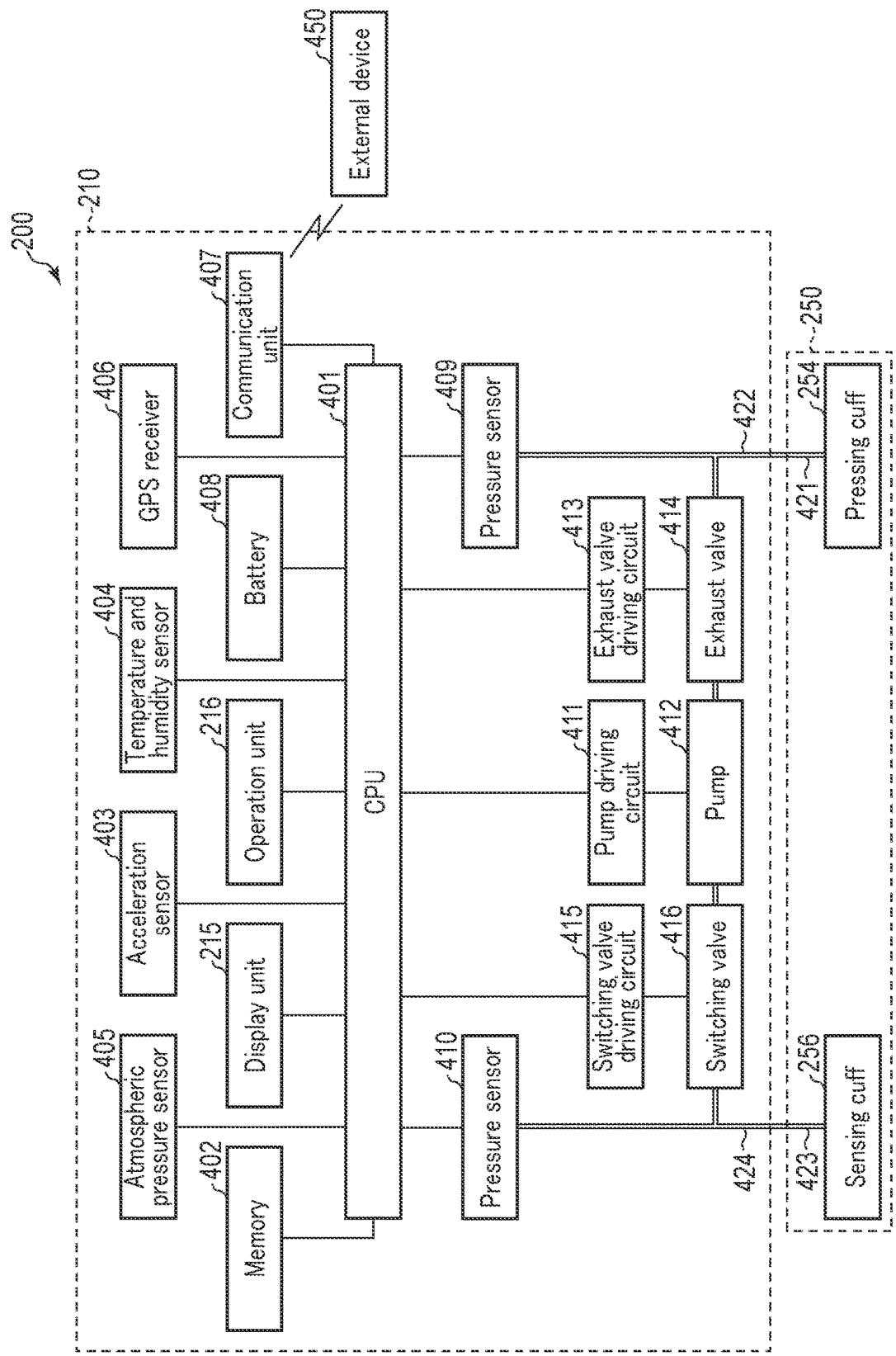
FIG. 4 is a block diagram showing an example of a hardware configuration of the blood pressure monitor of FIG. 2.

FIG. 4 shows an example of a hardware configuration of the blood pressure monitor 200. In addition to the display unit 215 and operation unit 216 described above, the blood pressure monitor 200 includes a central processing unit (CPU) 401, a memory 402, an acceleration sensor 403, a temperature and humidity sensor 404, an atmospheric pressure sensor 405, a GPS receiver 406, a communication unit 407, a battery 408, a pressure sensor 409, a pressure sensor 410, a pump driving circuit 411, a pump 412, an exhaust valve driving circuit 413, an exhaust valve 414, a switching valve driving circuit 415, and a switching valve 416, which are provided inside the main body 210 of the blood pressure monitor 200.

The CPU 401 is an example of a processor forming a computer. The CPU 401 controls each component according to a control program stored in the memory 402. For example, the CPU 401 performs control for driving the pump 412 and the switching valve 416 based on signals from the pressure sensors 409 and 410. Further, the CPU 401 performs control for calculating a blood pressure value and a pulse based on the signal from the pressure sensor 410.

The memory 402 includes, for example, a random access memory (RAM) and an auxiliary storage device. The auxiliary storage device stores various data items including data used for controlling each component of the blood pressure monitor 200 and blood pressure data obtained by blood pressure measurement, together with the above-described control program. The auxiliary storage device may be a semiconductor memory such as a flash memory. The RAM is used as a work memory when the program is executed. The memory 402 may further include a read only memory (ROM). In this case, a part or all of the control program may be stored in the ROM.

The acceleration sensor 403 is, for example, a three-axis acceleration sensor. The acceleration sensor 403 outputs, to the CPU 401, an acceleration signal representing accelerations in three directions orthogonal to each other. Based on the acceleration signal, the CPU 401 may calculate an amount of activity of the user. The amount of activity is an index related to a physical activity of the user such as walking, housework, and desk work. Examples of the amount of activity include the number of steps, the number of fast walking steps, the number of stair climbing steps, a walking distance, a calorie consumption, a fat burning amount, and the like. The CPU 401 may also estimate a sleeping state of the user by detecting a rolling over state of the user based on the acceleration signal.

The temperature and humidity sensor 404 measures an ambient temperature and humidity around the blood pressure monitor 200. The temperature and humidity sensor 404 outputs environmental data representing the environmental temperature and humidity to the CPU 401. The CPU 401 stores the environment data in the memory 402 in association with information of the measurement time. For example, the temperature (change in temperature) is considered to be one factor that may cause a blood pressure fluctuation in a human. Therefore, the environmental data is information that may be a factor of the blood pressure fluctuation of the user.

The atmospheric pressure sensor 405 detects an atmospheric pressure. The atmospheric pressure sensor 405 outputs atmospheric pressure data to the CPU 401. The atmospheric pressure data may be used to calculate the amount of activity. By using the atmospheric pressure data together with the acceleration signal, it is possible to more accurately calculate the number of stair-climbing steps, etc.

The GPS receiver 406 receives GPS signals transmitted from a plurality of GPS satellites, and outputs the received GPS signals to the CPU 401. The CPU 401 calculates position information of the blood pressure monitor 200, that is, a position of the user who is wearing the blood pressure monitor 200, based on the GPS signals. The blood pressure monitor 200 may not include the GPS receiver 406. In this case, the blood pressure monitor 200 may acquire from an external device 450 position information of the blood pressure monitor 200 calculated by the external device 450 via the communication unit 407.

The communication unit 407 is an interface for communicating with the external device 450. The external device 450 is, for example, a mobile terminal such as a smartphone or a tablet terminal, or a server. The communication unit 407 exchanges information with the external device 450 via a network. The communication unit 407 transmits information received from the CPU 401 to the external device 450. The communication unit 407 receives information from the external device 450, and passes the received information to the CPU 401. The communication via the network may be implemented by wireless communication, wired communication, or both. The network is, for example, the Internet, but is not limited to this. The network may be another type of network such as an in-hospital local area network (LAN), or may be one-to-one communication using a USB cable or the like. The communication unit 407 may include a micro USB connector. The communication unit 407 may directly communicate with the external device 450 by short-range wireless communication such as Bluetooth (registered trademark).

The battery 408 is, for example, a rechargeable second battery. The battery 408 supplies power to each component mounted on the main body 210. The battery 408 supplies power to, for example, the display unit 215, the CPU 401, the memory 402, the acceleration sensor 403, the temperature and humidity sensor 404, the atmospheric pressure sensor 405, the GPS receiver 406, the communication unit 407, the pressure sensor 409, the pressure sensor 410, the pump driving circuit 411, the pump 412, the exhaust valve driving circuit 413, the exhaust valve 414, the switching valve driving circuit 415, and the switching valve 416.

The pressure sensor 409 is, for example, a piezoresistive pressure sensor. The pressure sensor 409 detects a pressure inside the pressing cuff 255 via the flexible tube 421 and a channel member 422. The flexible tube 421 and the channel member 422 form a channel connecting the pump 412 and the pressing cuff 255 so as to allow the fluid from the pump 412 to be injected into the pressing cuff 255. The pressure sensor 409 outputs pressure data to the CPU 401. Although not shown in FIG. 4, between the pressure sensor 409 and the CPU 401, there are an amplifier that amplifies the output signal of the pressure sensor 409, and an analog-to-digital converter that converts the output signal of the amplifier from an analog signal to a digital signal.

The pressure sensor 410 is, for example, a piezoresistive pressure sensor. The pressure sensor 410 detects the pressure inside the sensing cuff 257 via the channel member 422, the flexible tube 423, and the channel member 424. The channel member 422, the flexible tube 423, and the channel member 424 form a channel that connects the pump 412 and the sensing cuff 257 to allow fluid from the pump 412 to be injected into the sensing cuff 257. The pressure sensor 410 outputs pressure data to the CPU 401. Although not shown in FIG. 4, between the pressure sensor 410 and the CPU 401, there are an amplifier that amplifies the output signal of the pressure sensor 410, and an analog-to-digital converter that converts the output signal of the amplifier from an analog signal to a digital signal.

The pump driving circuit 411 drives the pump 412 based on a control signal from the CPU 401. The pump 412 is, for example, a piezoelectric pump. The pump 412 can supply the fluid to the pressing cuff 255 through the flexible tube 421 and the channel member 422. Further, the pump 412 can supply the fluid to the sensing cuff 257 through the channel member 422, the flexible tube 423, and the channel member 424.

The exhaust valve driving circuit 413 drives the exhaust valve 414 based on the control signal from the CPU 401. The exhaust valve 414 is provided at the channel member 422. The opening and closing (opening degree) of the exhaust valve 414 is controlled based on the control signal from the CPU 401. When the pump 412 is activated, the exhaust valve 414 is closed. When in an open state, the exhaust valve 414 exhausts the air inside the pressing cuff 255 and the sensing cuff 257 to the atmosphere. The exhaust valve 414 has a function of a check valve, and the exhausted air does not flow back.

The switching valve driving circuit 415 drives the switching valve 416 based on the control signal from the CPU 401. The switching valve 416 is interposed between the channel member 422 and the channel member 424. The switching valve 416 is, for example, a normally open electromagnetic valve. The opening/closing (opening degree) of the switching valve 416 is controlled based on the control signal from the CPU 401. When the switching valve 416 is in an open state, the pump 412 can supply the fluid to the sensing cuff 257 through the channel member 422, the flexible tube 423, and the channel member 424. The switching valve 416 may be a three-way cock, and the channel members 422 and 424 may be connected to the pump 412 via the switching valve 416.

The pump driving circuit 411, the pump 412, the exhaust valve driving circuit 413, the exhaust valve 414, the switching valve driving circuit 415, and the switching valve 416 are an example of a fluid supply unit that supplies the fluid to the pressing cuff 255 and the sensing cuff 257 and exhausts the fluid from the pressing cuff 255 and the sensing cuff 257.

Figure 5:
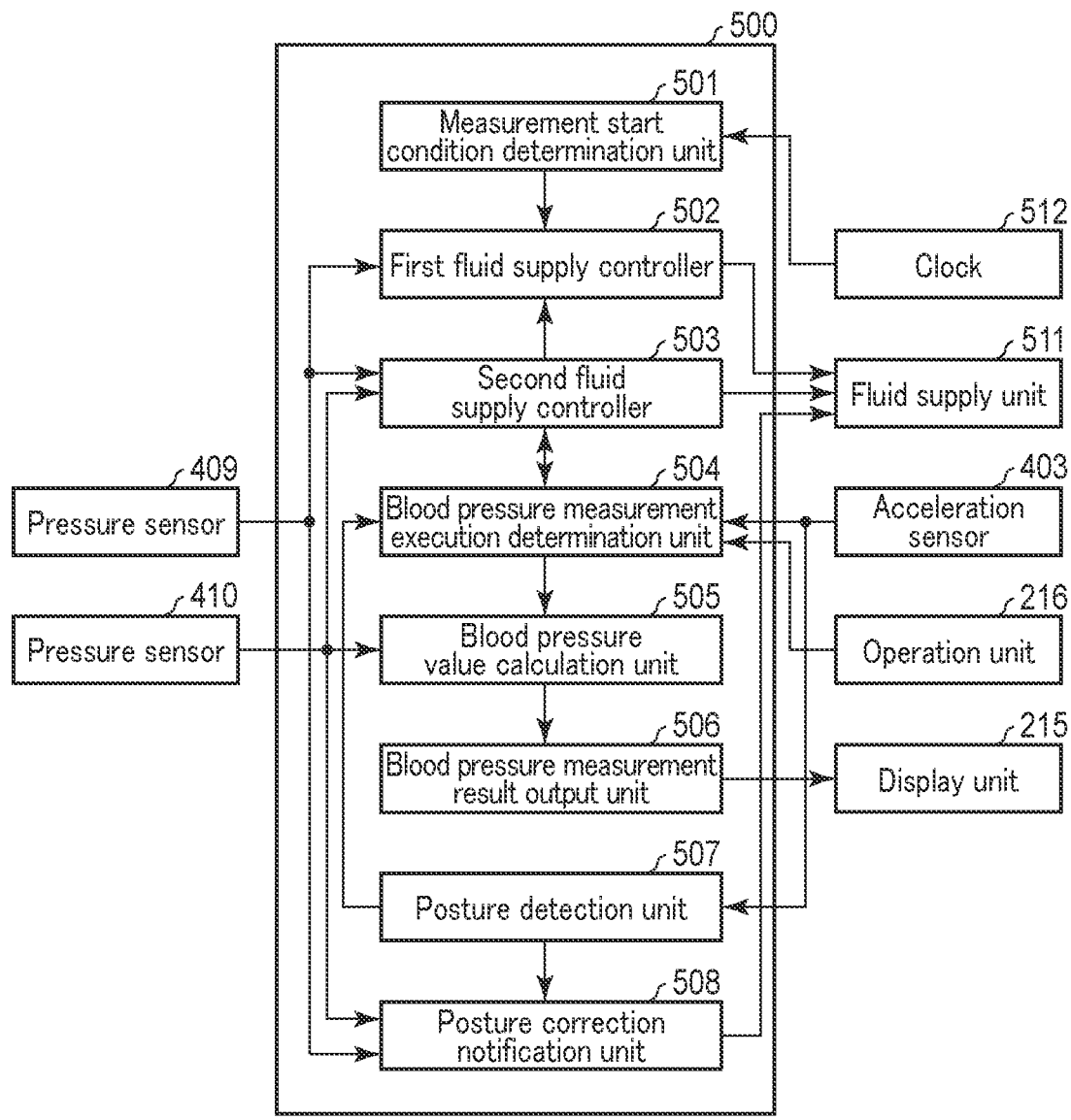
FIG. 5 is a functional block diagram showing a controller included in the blood pressure monitor of FIG. 4.

FIG. 5 is a block diagram illustrating a configuration of software executed by the controller. In FIG. 5, the same parts as those in FIG. 4 are denoted by the same reference numerals, and detailed description thereof will be omitted.

The controller 500 is realized by one or more general-purpose processors (for example, the CPU 401) executing a control program stored in the memory 402. A part or all of the controller 500 may be realized by a hardware circuit such as an application specific integrated circuit (ASIC) or a field programmable gate array (FPGA).

The control program executed by the controller 500 includes a measurement start condition determination unit 501, a first fluid supply controller 502, a second fluid supply controller 503, a blood pressure measurement execution determination unit 504, a blood pressure value calculation unit 505, and a blood pressure measurement result output unit 506.

The measurement start condition determination unit 501 determines whether or not a situation of the user satisfies the first condition (measurement start condition) in which vital information measurement is recommended. For example, the measurement start condition determination unit 501 determines whether or not a current time indicated by the clock 512 has reached a predetermined measurement time. Alternatively, the measurement start condition determination unit 501 may determine whether or not a current position of the blood pressure monitor 200 calculated based on the GPS signal received by the GPS receiver 406 coincides with a predetermined position, for example, corresponding to a workplace, or may determine whether or not the current time has reached a start time of an event such as a conference registered in a scheduler (not shown). The measurement start condition determination unit 501 may determine whether or not the atmospheric pressure detected by the atmospheric pressure sensor 405 or the temperature and humidity detected by the temperature and humidity sensor 404 has exceeded a predetermined range, or may determine whether or not the user's heart rate has rapidly increased at a certain increase rate or more.

When it is determined that any of the above-described various states relating to the user satisfies the measurement start condition, the measurement start condition determination unit 501 gives the first fluid supply controller 502 a trigger for reporting that the measurement start timing has come.

Upon receiving the trigger from the measurement start condition determination unit 501, the first fluid supply controller 502 controls the fluid supply unit 511 to supply the fluid to, for example, the pressing cuff 255 from among the pressing cuff 255 and the sensing cuff 257. That is, the first fluid supply controller 502 performs control (notification control) for reporting that the measurement start timing has come. Alternatively, the first fluid supply controller 502 may control the fluid supply unit 511 to supply the fluid to the sensing cuff 257. The first fluid supply controller 502 may control the fluid supply unit 511 to supply the fluid to both the pressing cuff 255 and the sensing cuff 257.

The fluid supply unit 511 includes the pump driving circuit 411, the pump 412, the exhaust valve driving circuit 413, the exhaust valve 414, the switching valve driving circuit 415, the switching valve 416, the channel member 422, and the channel member 424. The first fluid supply controller 502 provides control signals to the pump driving circuit 411, the exhaust valve driving circuit 413, and the switching valve driving circuit 415.

The blood pressure measurement execution determination unit 504 determines whether or not the second condition indicating that the user is in a measurable state is satisfied after the supply control is performed by the second fluid supply controller 502.

Figure 6:
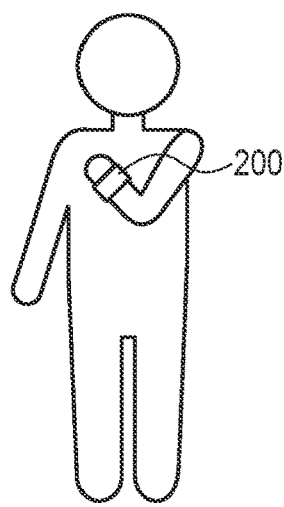
FIG. 6 is a view showing an example of a preferred blood pressure measurement posture.

In general, in order to accurately measure the blood pressure, it is desirable to measure the blood pressure in a posture in which the position of the measurement site (the left wrist in this example) is adjusted to the height of the heart. Therefore, the control program executed by the controller 500 may further include a posture detection unit 507 that detects the posture of the user. The posture detection unit 507 detects a state in which the user is in a posture suitable for measurement, as illustrated in FIG. 6, for example. The posture suitable for the measurement can be detected based on the three-axis acceleration signal obtained by the acceleration sensor 403. Note that the blood pressure monitor 200 may further include an angular velocity sensor (not shown), and in this case, the posture detection unit 507 may detect the state in which the user is in a posture suitable for measurement based on the acceleration signal and the output signal of the angular velocity sensor. When detecting a state in which the user is in a posture suitable for measurement, the posture detection unit 507 provides the blood pressure measurement execution determination unit 504 with a notification indicating the same. Upon receiving the notification, the blood pressure measurement execution determination unit 504 determines that the blood pressure measurement has become possible.

The controller 500 may further include a posture correction notification unit 508 that notifies the user to correct the posture of the user to a posture suitable for measurement in response to the posture detection unit 507 detecting that the posture of the user is different from the posture suitable for measurement. The notification to prompt the posture correction is performed by, for example, injection of the fluid into the cuff, a display, or the like. As an example, the posture correction notification unit 508 functions as a third fluid supply controller that controls the injection of the fluid into the cuff in a compression mode different from that of the first fluid supply controller 502. For example, the posture correction notification unit 508 controls the fluid supply unit 511 so that the cuff repeats inflation and deflation. For notification to prompt the posture correction, the pressing cuff 255, the sensing cuff 257, or both may be used.

In another example, the blood pressure measurement execution determination unit 504 may determine that the blood pressure measurement is possible when the user's posture enters a measurable state and the user inputs a blood pressure measurement start instruction using the operation unit 216. For example, when the user presses the button 216A shown in FIG. 2, the blood pressure measurement execution determination unit 504 determines that the blood pressure measurement is possible.

When it is determined that the user enters a state suitable for measurement, the blood pressure measurement execution determination unit 504 sends to the second fluid supply controller 503 a trigger for executing the blood pressure measurement.

Upon receiving the trigger for executing the blood pressure measurement, the second fluid supply controller 503 controls the fluid supply unit 511 to supply the fluid to both the pressing cuff 255 and the sensing cuff 257. That is, control for executing the blood pressure measurement (execution control) is performed. In the execution control, the fluid may be supplied to the pressing cuff 255 from among the pressing cuff 255 and the sensing cuff 257.

In addition, the first fluid supply controller 502 determines that the user did not notice the notification when the blood pressure measurement execution determination unit 504 cannot determine within a predetermined time after the notification control that the user is in a state suitable for measurement. Then, in order to notify the user again that the measurement start timing has come, the fluid supply unit 511 is controlled to supply the fluid to the pressing cuff 255.

The blood pressure value calculation unit 505 calculates the blood pressure value based on pressure data of the sensing cuff 257 obtained by the pressure sensor 410 with the measurement site being compressed by supplying the fluid to the pressing cuff 255 and the sensing cuff 257 under the control of the second fluid supply controller 503. The blood pressure value includes, for example, but is not limited to, systolic blood pressure (SBP) and diastolic blood pressure (DBP). The calculated blood pressure value is stored in the memory 402 in association with the time, temperature, humidity, wrist height, posture, and the like.

The blood pressure measurement result output unit 506 outputs a blood pressure measurement result. For example, the blood pressure measurement result output unit 506 displays the blood pressure value calculated by the blood pressure value calculation unit 505 on the display unit 215.

(Operation)

Next, the operation of the blood pressure monitor 200 will be described.

Figure 7:
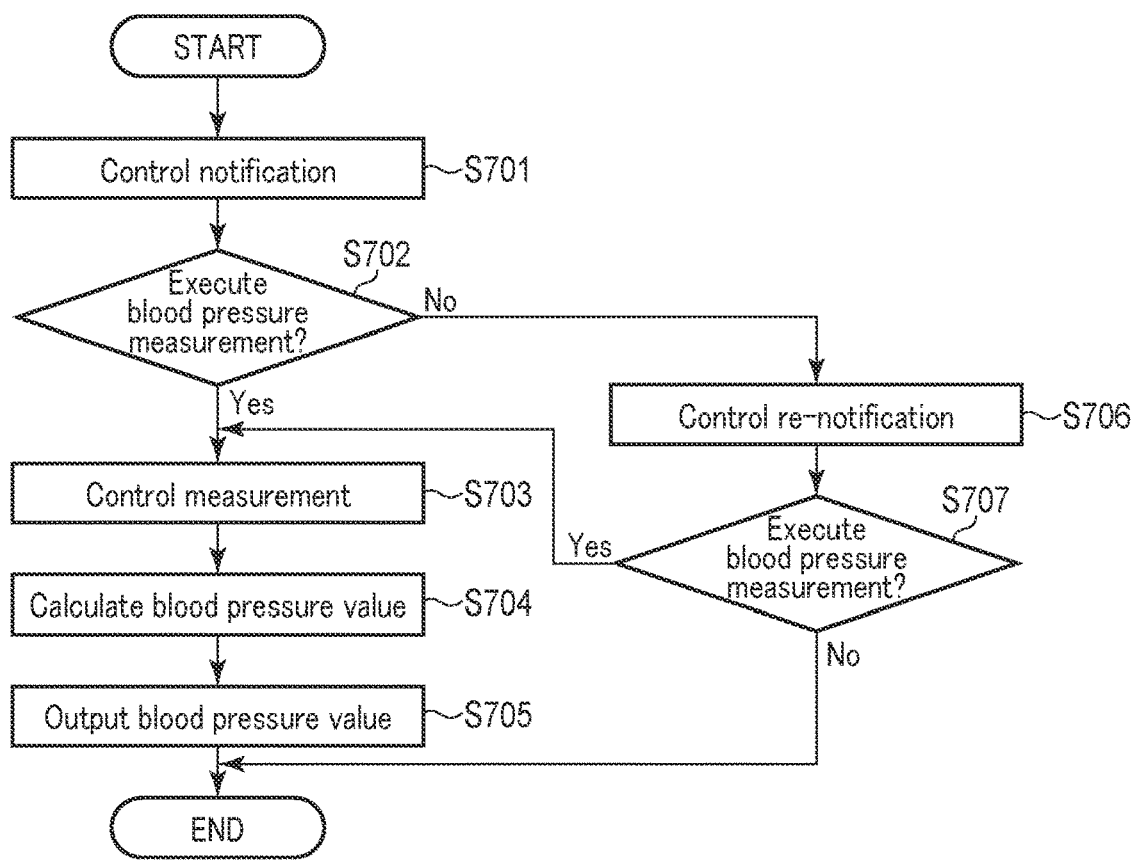
FIG. 7 is a flowchart illustrating a method of measuring blood pressure according to the first embodiment.

FIG. 7 shows a procedure example of a blood pressure measurement method according to the first embodiment. Here, it is assumed that the blood pressure monitor 200 is worn by the user. It is also assumed that the fluid is air.

In step S701 of FIG. 7, the first fluid supply controller 502 receives the trigger for reporting that the measurement start timing has come from the measurement start condition determination unit 501, and performs control for reporting that the measurement start timing has come (notification control). In the notification control, air is supplied to at least one of the pressing cuff 255 and the sensing cuff 257. The notification control is triggered, for example, when the current time reaches a predetermined time. Thereafter, the blood pressure monitor 200 enters a blood pressure measurement standby state. That is, the state in which air is contained in the cuff (at least one of the pressing cuff 255 or the sensing cuff 257) is maintained. Here, air supplied to such an extent that the user can recognize the inflation of the cuff is sufficient, and it is not necessary to strongly inflate the cuff as in the blood pressure measurement.

In step S702, the blood pressure measurement execution determination unit 504 determines whether to execute blood pressure measurement. If the blood pressure measurement execution determination unit 504 determines that the blood pressure measurement should be executed in step S702, the process proceeds to step S703. For example, in response to the posture detection unit 507 detecting that the user is in a posture suitable for measurement, the blood pressure measurement execution determination unit 504 determines that blood pressure measurement should be executed. If the blood pressure measurement execution determination unit 504 does not determine that the blood pressure measurement should be executed by the time a predetermined time elapses (for example, 30 seconds) after the process of step S701 is executed, the process proceeds to step S706.

In step S706, the first fluid supply controller 502 performs control again for reporting that the measurement start timing has come (re-notification control). In the re-notification control, air is supplied to at least one of the pressing cuff 255 or the sensing cuff 257. In step S707, the blood pressure measurement execution determination unit 504 determines whether to execute the blood pressure measurement. If the blood pressure measurement execution determination unit 504 determines that blood pressure measurement should be executed in step S707, the process proceeds to step S703. If the blood pressure measurement execution determination unit 504 does not determine that the blood pressure measurement should be executed by the time a predetermined time elapses after the process of step S705 is executed, the process ends without executing the blood pressure measurement.

If the blood pressure measurement execution determination unit 504 determines that the blood pressure measurement should be executed in step S702 or step S707, the process proceeds to step S703. In step S703, the blood pressure measurement is started. Specifically, the second fluid supply controller 503 performs control for executing blood pressure measurement (measurement control). In the measurement control, air is supplied to the pressing cuff 255 or both the pressing cuff 255 and the sensing cuff 257.

In step S704, the blood pressure value calculation unit 505 calculates a blood pressure value based on pressure data from the pressure sensor 410. When the blood pressure value is calculated, the second fluid supply controller 503 performs control for exhausting air in the pressing cuff 255 and the sensing cuff 257.

In step S705, the blood pressure measurement result output unit 506 displays the blood pressure value calculated by the blood pressure value calculation unit 505 on the display unit 215.

In the process of step S702 or step S707, if an interruption instruction is input by the user, the blood pressure measurement execution determination unit 504 may continue the process of determining whether to start blood pressure measurement even after a predetermined time has elapsed. For example, when the user presses the button 216B, the blood pressure measurement execution determination unit 504 can continue the determination process until a next instruction (for example, a measurement start instruction) is input by the user. In step S702 or step S707, if a cancel instruction is input by the user, the process may be ended without executing the blood pressure measurement. For example, the user can stop the blood pressure measurement by pressing the button 216C.

With reference to FIG. 8, a series of flows from when the measurement start condition is satisfied to when the blood pressure measurement is completed will be specifically described.

In step S801, when the current time reaches a predetermined time, initialization is performed. Specifically, the processing memory area of the memory 402 is initialized. Further, with the switching valve 416 maintained in an open state, the first fluid supply controller 502 turns off the pump 412 via the pump driving circuit 411 and opens the exhaust valve 414 via the exhaust valve driving circuit 413. In this manner, air inside the pressing cuff 255 and the sensing cuff 257 is exhausted. The output values at the current moment of the pressure sensors 409 and 410 are set as reference values (0 mmHg adjustment).

In step S802, the first fluid supply controller 502 closes the exhaust valve 414 via the exhaust valve driving circuit 413, and turns on the pump 412 via the pump driving circuit 411. In this manner, the supply of air to the pressing cuff 255 and the sensing cuff 257 is started. The pressures of the pressing cuff 255 and sensing cuff 257 are monitored using the pressure sensors 409 and 410.

In step S803, when an appropriate amount of air is contained in the sensing cuff 257, the first fluid supply controller 502 closes the switching valve 416 via the switching valve driving circuit 415. For example, the first fluid supply controller 502 closes the switching valve 416 via the switching valve driving circuit 415 when the pressure of the sensing cuff 257 reaches a predetermined pressure (for example, 15 mmHg) or when a predetermined time of the driving time of the pump 412 has elapsed (for example, 3 seconds). The supply of air to the pressing cuff 255 is continued.

In step S804, the first fluid supply controller 502 turns off the pump 412 via the pump driving circuit 411 when the pressure of the pressing cuff 255 reaches a predetermined pressure (for example, 30 mmHg) or a predetermined time of the driving time of the pump 412 has elapsed (for example, 5 seconds). At this time, the exhaust valve 414 is kept closed.

Subsequently, the blood pressure measurement execution determination unit 504 determines whether to execute the blood pressure measurement. Here, it is assumed that the user takes a posture suitable for measurement, and in response to this, the blood pressure measurement execution determination unit 504 determines that the blood pressure measurement should be executed (step S805).

Figure 9:
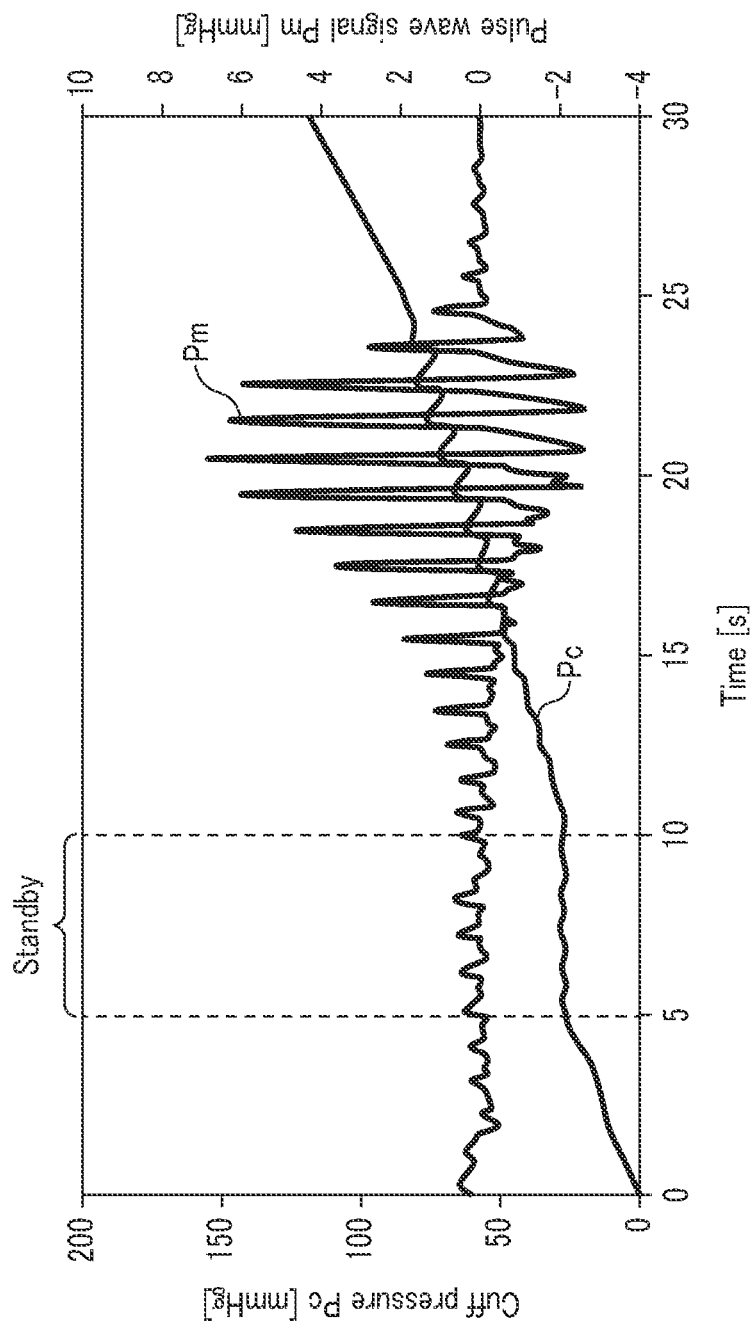
FIG. 9 is a graph showing an example of pressure Pc of a sensing cuff and pulse wave signal Pm detected by a pressure sensor shown in FIG. 4.

In step S806, the second fluid supply controller 503 turns on the pump 412 via the pump driving circuit 411 with the switching valve 416 being closed. As a result, air is further supplied to the pressing cuff 255, and the pressing cuff 255 is inflated and gradually pressurized. At this time, the back plate 256 transmits the pressing force from the pressing cuff 255 to the sensing cuff 257. In this manner, the sensing cuff 257 compresses the left wrist. In the pressurization process, in order to calculate the blood pressure value, the controller 500 monitors pressure Pc of the sensing cuff 257 using the pressure sensor 410, and acquires the fluctuation component of the arterial volume generated in the radial artery of the wrist as pulse wave signal Pm as shown in FIG. 9. In FIG. 9, a time interval of 0 to 5 seconds relates to the notification control, and the blood pressure measurement is started from the time point of 10 seconds.

In step S807, the blood pressure value calculation unit 505 attempts to calculate a blood pressure value by applying a well-known algorithm by an oscillometric method based on the pulse wave signal Pm acquired at this time period. At this time, if the blood pressure value cannot be calculated yet due to insufficient data, the supply of air to the pressing cuff 255 is continued as long as the pressure Pc of the sensing cuff 257 has not reached the upper limit pressure (predetermined to be, for example, 300 mmHg for safety).

When the blood pressure value is calculated in this manner, in step S808, the second fluid supply controller 503 turns off the pump 412 via the pump driving circuit 411, opens the exhaust valve 414 via the exhaust valve driving circuit 413, and opens the switching valve 416 via the switching valve driving circuit 415. Accordingly, the air in the pressing cuff 255 and the sensing cuff 257 is exhausted.

The blood pressure may be calculated not in the pressurization process of the pressing cuff but in the depressurization process.

In step S809, the blood pressure value obtained as a result of the blood pressure measurement is displayed on the display unit 215. The processes in steps S801 to S704 correspond to the notification control in step S701 shown in FIG. 7, and the process in step S806 corresponds to the measurement control in step S703 shown in FIG. 7.

(Advantageous Effects)

As described above, the blood pressure monitor 200 according to the first embodiment includes the first fluid supply controller 502 that, when the user's situation satisfies the first condition (measurement start condition) in which the blood pressure measurement is recommended, controls the supply of the fluid to the cuff by the fluid supply unit 511 to compress the left wrist in the first compression mode for informing the user that the first condition is satisfied. Thus, when the user's situation satisfies the first condition in which the vital information measurement is recommended, the subject is notified accordingly by the compression with the cuff. Therefore, the user can reliably recognize that the measurement is recommended. Moreover, since notification is given by inflation of the cuff, which is already provided for measurement, it is not necessary to provide other notification means such as light, sound, vibration, etc.

The first fluid supply controller 502 may perform control for compressing the left wrist in the first compression mode when at least one of a preset time of day, place, or event is satisfied as the first condition. Accordingly, when at least one of a preset time of day, place, or event is satisfied, a notification to prompt measurement of vital information is made.

The blood pressure monitor 200 further includes a second fluid supply control unit that controls the supply of the fluid to the cuff by the fluid supply unit to compress the left wrist in the second compression mode to measure the blood pressure when the second condition indicating that the user is in a measurable state is satisfied after the control by the first fluid supply controller 502. Thus, after the notification, when the user is in a measurable state, the blood pressure measurement is performed. Therefore, accurate measurement can always be performed. In addition, since a certain amount of fluid is contained in the cuff through the fluid supply in the first compression mode, the fluid supply in the second compression mode requires a smaller amount of fluid than the amount necessary for normal blood pressure measurement. That is, the time required for blood pressure measurement is shortened. As a result, it is possible to reduce burdens on the user, e.g., shortening the time during which the user maintains the measurement posture.

The first compression mode in the first fluid supply controller 502 is set to a pressure value smaller than that of the second compression mode in the second fluid supply controller 503. Thus, the cuff pressure at the time of the notification is set to a value smaller than that at the time of measurement. Therefore, the notification can be made without applying a large physical load to the subject, and an electric power consumed for inflating the cuff for the notification can be reduced.

The cuff includes the pressing cuff 255 and the sensing cuff 257. The first fluid supply controller 502 may control the fluid supply unit 511 to supply the fluid to one of the pressing cuff 255 and the sensing cuff 257, and the second fluid supply controller 503 may control the fluid supply unit 511 to supply the fluid to both the pressing cuff 255 and the sensing cuff 257. In this case, the notification and the measurement can be distinguished from each other by selecting the fluid bladders (the pressing cuff 255 and the sensing cuff 257), and thus it is not necessary to differentiate the pressure between the notification and the measurement as in the case of using one fluid bladder, for example.

The blood pressure monitor 200 may further include a posture detection unit 507 that detects the posture of the user. In this case, when the posture detection unit 507 detects that the posture of the user becomes a preset posture in which measurement can be taken as the second condition, the second fluid supply controller 503 performs control for compressing the left wrist in the second compression mode. Accordingly, since the measurement is performed when the posture of the user becomes a posture in which measurement can be taken, the measurement can always be performed when the posture of the user is in an appropriate state. As a result, the blood pressure can be accurately measured. When the blood pressure monitor 200 includes the posture correction notification unit 508 in addition to the posture detection unit 507, it is possible to prompt the user to take a posture suitable for measurement.

The blood pressure monitor 200 may further include an input detection unit that detects an input of operation information indicating that the user is in a measurable state. In this case, when the input detector detects the input of the operation information as the second condition, the second fluid supply controller 503 may perform control for compressing the left wrist in the second compression mode. In this case, since the measurement is performed when the operation information indicating that the user is in a measurable state is input, for example, the measurement can be performed after the user enters an environment or timing suitable for the measurement.

Also, because the fluid supply can be quiet, the notification by inflation of the cuff is less noticeable to people around the user than a notification by sound or vibration. Therefore, if the user moves to a place where there is no person around and then performs blood pressure measurement, blood pressure measurement can be performed without being noticed by anyone.

When the second condition is not satisfied within a predetermined time after the control for compressing the left wrist in the first compression mode, the first fluid supply controller 502 may perform control again for compressing the left wrist in the second compression mode. As a result, when the user is not in a measurable state even after a certain period of time has elapsed since the notification, the notification is performed again. Therefore, even when the user does not notice the notification for some reason, it is possible to notify the user that the condition of measurement has been reached.

Other Embodiments

The present invention is not limited to the above embodiment. For example, the sensing cuff 257 may be filled with a fluid at the manufacturing stage of the cuff structure 250. In this case, the fluid from the pump 412 is supplied only to the pressing cuff 255. In other words, it is not necessary to control the supply of the fluid to the sensing cuff 257 every time the blood pressure measurement is performed. As a result, the CPU load can be reduced. The fluid supplied to the pressing cuff 255 and the sensing cuff 257 may be different. A structure in which the pressing cuff 255 faces the sensing cuff 257 via the measurement site in the worn state may be employed.

Further, the blood pressure monitor may adopt a single cuff structure having one cuff. If a single cuff construction is employed, then construction and control are facilitated. As a result, the manufacturing cost can be suppressed and the CPU load can be reduced. Further, the blood pressure monitor may employ a structure having three or more cuffs.

The present invention is not limited to the above-described embodiments as they are, and can be embodied by modifying the components without departing from the scope of the invention at the implementation stage. Further, various inventions can be formed by appropriately combining components disclosed in the above embodiments. For example, some of the components may be deleted from each of the embodiments. In addition, the components between different embodiments may be combined as appropriate.

Part or all of the above-mentioned embodiments may also be described as in the following additional notes, without limitation thereto.

(Additional Description 1)

A vital information measuring apparatus for measuring vital information by supplying a fluid from a fluid supply unit to a cuff to compress a measurement site of a subject, the apparatus comprising:
at least one processor; and
a memory coupled to the at least one processor,
wherein the at least one processor is configured to control, when a situation of the subject satisfies a first condition in which measurement of the vital information is recommended, a supply of the fluid to the cuff by the fluid supply unit to compress the measurement site in a first compression mode for notifying the subject that the first condition is satisfied.

(Additional Description 2)

A method of measuring vital information executed by a vital information measuring apparatus configured to measure vital information by supplying a fluid from a fluid supply unit to a cuff to compress a measurement site of a subject, the method comprising:
controlling, when a situation of the subject satisfies a first condition in which measurement of the vital information is recommended, a supply of the fluid to the cuff by the fluid supply unit to compressing the measurement site in a first compression mode for notifying the subject that the first condition is satisfied, by using at least one processor.

REFERENCE SIGNS LIST 1. vital information measuring apparatus
2. cuff
10. vital information measuring unit
20. fluid supply unit
30. first fluid supply controller
40. second fluid supply controller
200. blood pressure monitor
210. main body
211. case
212. glass
213. back cover
215. display unit
216. operation unit
216A, 216B, 216C. push button
221. connecting rod
226. connecting rod
230. belt
231. first belt portion
232. proximal part
233. distal part
234, 235. belt holder
236. second belt portion
237. proximal part
238. distal part
239. small opening
240. buckle
241. frame
242. bar
243. connecting rod
250. cuff structure
251. proximal part
252. distal part 254. curler
255. pressing cuff
256. back plate
257. sensing cuff
300. left wrist
300A. artery passing portion
301. radial artery
302. ulnar artery
303. radius
304. ulna
305. tendon
401. CPU
402. memory
403. acceleration sensor
404. temperature and humidity sensor
405. atmospheric pressure sensor
406. GPS receiver
407. communication unit
408. battery
409. pressure sensor
410. pressure sensor
411. pump driving circuit
412. pump
413. exhaust valve driving circuit
414. exhaust valve
415. switching valve driving circuit
416. switching valve
421. flexible tube
422. channel member
423. flexible tube
424. channel member
450. external device
500. controller
501. measurement start condition determination unit
502. first fluid supply controller
503. second fluid supply controller
504. blood pressure measurement execution determination unit
505. blood pressure value calculation unit
506. blood pressure measurement result output unit
507. posture detection unit
508. posture correction notification unit
511. fluid supply unit
512. clock

The invention claimed is:

1. A vital information measuring apparatus for measuring vital information by compressing a measurement site of a subject with a cuff, the apparatus comprising:
  a fluid supply unit configured to supply a fluid to the cuff; and
  a processor configured to control, when a situation of the subject satisfies a first condition in which measurement of the vital information is recommended, a supply of the fluid to the cuff by the fluid supply unit to compress the measurement site in a first compression mode for informing the subject that the first condition is satisfied.

2. The vital information measuring apparatus according to claim 1, wherein when, as the first condition, at least one of a predetermined time of day, place, or event is satisfied, the processor performs control for compressing the measurement site in the first compression mode.

3. The vital information measuring apparatus according to claim 1, wherein the processor is further configured to control, when a second condition indicating that the subject is in a measurable state is satisfied after compression in the first compression mode, the supply of the fluid to the cuff by the fluid supply unit to compress the measurement site in a second compression mode for measuring the vital information.

4. The vital information measuring apparatus according to claim 3, wherein the processor sets the first compression mode to a pressure value smaller than that of the second compression mode.

5. The vital information measuring apparatus according to claim 3, wherein the cuff includes a first fluid bladder and a second fluid bladder, and
  the processor controls the fluid supply unit to supply the fluid to one of the first fluid bladder or the second fluid bladder in the first compression mode, and controls the fluid supply unit to supply the fluid to both the first fluid bladder and the second fluid bladder in the second compression mode.

6. The vital information measuring apparatus according to claim 3, wherein the processor is further configured to detect a posture of the subject, and
  wherein, when, as the second condition, the posture detection unit detects that the posture of the subject is a predetermined posture in which measurement can be taken, the processor performs control for compressing the measurement site in the second compression mode.

7. The vital information measuring apparatus according to claim 6, wherein the processor is further configured to notify the subject to correct the posture of the subject when the processor detects that the posture of the subject is different from the posture in which measurement can be taken.

8. The vital information measuring apparatus according to claim 3, wherein the processor is further configured to detect an input of operation information indicating that the subject is in a measurable state, and
  wherein when, as the second condition, the processor detects the input of operation information, the processor performs control for compressing the measurement site in the second compression mode.

9. The vital information measuring apparatus according to claim 3, wherein when the second condition is not satisfied within a predetermined time period after the control for compressing the measurement site in the first compression mode, the processor performs the control for compressing the measurement site in the first compression mode again.

10. A vital information measurement method executed by a vital information measuring apparatus configured to measure vital information by supplying a fluid from a fluid supply unit to a cuff to compress a measurement site of a subject, the method comprising:
  controlling, when a situation of the subject satisfies a first condition in which measurement of the vital information is recommended, a supply of the fluid to the cuff by the fluid supply unit to compress the measurement site in a first compression mode for informing the subject that the first condition is satisfied.

11. The vital information measurement method according to claim 10, further comprising controlling, when a second condition indicating that the subject is in a measurable state is satisfied after the control for compressing the measurement site in the first compression mode, the supply of the fluid to the cuff by the fluid supply unit to compress the measurement site in a second compression mode for measuring the vital information.

12. A non-transitory computer readable medium including computer executable instructions, wherein the instructions, when executed by a processor, cause the processor to perform a vital information measurement method executed by a vital information measuring apparatus configured to measure vital information by supplying a fluid from a fluid supply unit to a cuff to compress a measurement site of a subject, the method comprising:
    controlling, when a situation of the subject satisfies a first condition in which measurement of the vital information is recommended, a supply of the fluid to the cuff by the fluid supply unit to compress the measurement site in a first compression mode for informing the subject that the first condition is satisfied.

\* \* \* \* \*